(12) United States Patent
Curti et al.

(10) Patent No.: US 7,640,932 B2
(45) Date of Patent: Jan. 5, 2010

(54) NASAL CANNULA FOR ACQUIRING BREATHING INFORMATION

(75) Inventors: James N. Curti, Bakersfield, CA (US); Peter W. Salter, Bakersfield, CA (US); James Chua, Bakersfield, CA (US)

(73) Assignee: Salter Labs, Arvin, CA (US)

( * ) Notice: Subject to any disclaimer, the term of this patent is extended or adjusted under 35 U.S.C. 154(b) by 715 days.

(21) Appl. No.: 11/155,901

(22) Filed: Jun. 17, 2005

(65) Prior Publication Data

US 2005/0284484 A1 Dec. 29, 2005

Related U.S. Application Data

(60) Continuation-in-part of application No. 10/627,502, filed on Jul. 25, 2003, now abandoned, which is a division of application No. 09/837,720, filed on Apr. 18, 2001, now Pat. No. 6,655,385, which is a continuation of application No. 09/184,111, filed on Nov. 2, 1998, now Pat. No. 6,439,234, which is a continuation of application No. PCT/US98/05573, filed on Apr. 3, 1998.

(60) Provisional application No. 60/045,080, filed on Apr. 29, 1997.

(51) Int. Cl.
*A61M 15/08* (2006.01)
*A61M 15/00* (2006.01)
*A61M 16/00* (2006.01)

(52) U.S. Cl. .......................... 128/204.23; 128/204.18; 128/204.21; 128/204.22; 128/207.18

(58) Field of Classification Search ............ 128/203.22, 128/204.18, 204.21–204.23, 206.11, 207.18, 128/203.18; 600/529, 532, 538
See application file for complete search history.

(56) References Cited

U.S. PATENT DOCUMENTS

| 2,693,800 | A | | 11/1954 | Caldwell |
| 3,643,660 | A | | 2/1972 | Hudson et al. |
| 4,156,426 | A | * | 5/1979 | Gold .................... 128/204.18 |
| 4,753,233 | A | | 6/1988 | Grimes |
| 4,958,075 | A | | 9/1990 | Mace et al. |
| 5,046,491 | A | * | 9/1991 | Derrick ................ 128/200.24 |
| 5,131,387 | A | * | 7/1992 | French et al. .......... 128/205.27 |
| 5,137,017 | A | * | 8/1992 | Salter .................... 128/207.18 |
| 5,299,118 | A | * | 3/1994 | Martens et al. ............ 600/509 |
| 5,335,656 | A | | 8/1994 | Bowe et al. |
| 5,626,131 | A | | 5/1997 | Chua et al. |

(Continued)

FOREIGN PATENT DOCUMENTS

WO 89/09565 10/1989

(Continued)

*Primary Examiner*—Justine R Yu
*Assistant Examiner*—Kristen C Matter
(74) *Attorney, Agent, or Firm*—Davis & Bujold, P.L.L.C.

(57) ABSTRACT

A method of monitoring breathing of a patient with a nasal cannula. The method comprising the steps of forming the nasal cannula with at least one nare, and at least one nare having a primary inlet/outlet opening formed in a remote end thereof. Coupling the nasal cannula to a detection device for monitoring breathing characteristics of the patient while the patient is sleeping. Detecting breathing characteristics of the patient, while the patient is sleeping, via at least the primary inlet/outlet opening of the nare and sending the detected breathing characteristics of the patient to detection device for evaluation.

18 Claims, 12 Drawing Sheets

U.S. PATENT DOCUMENTS

| | | |
|---|---|---|
| 5,664,567 A | 9/1997 | Linder |
| 5,682,881 A | 11/1997 | Winthrop et al. |
| 6,379,312 B2 * | 4/2002 | O'Toole ..................... 600/529 |
| 6,422,240 B1 * | 7/2002 | Levitsky et al. ........ 128/207.18 |
| 6,439,234 B1 * | 8/2002 | Curti et al. ............. 128/207.18 |
| 6,655,385 B1 * | 12/2003 | Curti et al. ............. 128/207.18 |
| 7,007,694 B2 | 3/2006 | Aylsworth et al. |
| 2005/0051176 A1 * | 3/2005 | Riggins ................. 128/207.18 |

FOREIGN PATENT DOCUMENTS

WO     WO 89/09565     10/1989

* cited by examiner

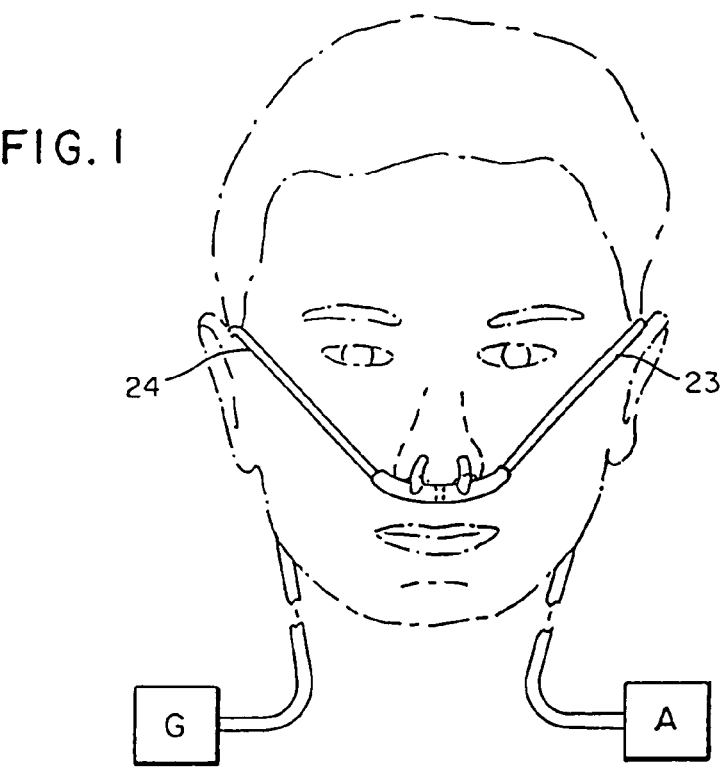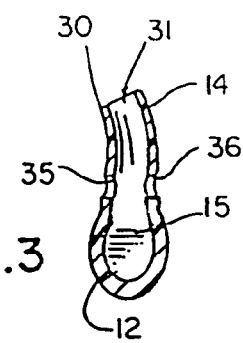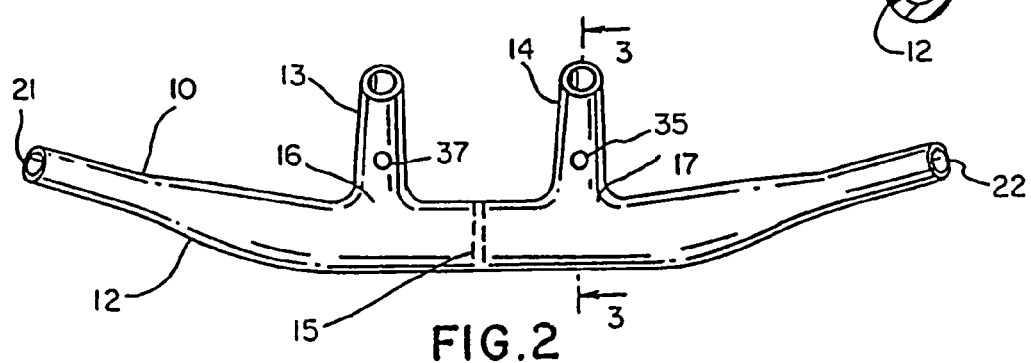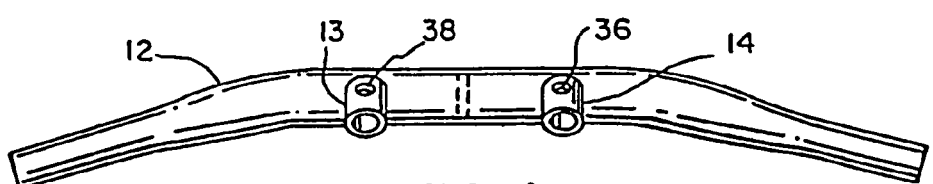

NASAL CANNULA FOR ACQUIRING BREATHING INFORMATION

This application is a continuation-in-part of patent application Ser. No. 10/627,502 filed Jul. 25, 2003 now abandoned which is a divisional of patent application Ser. No. 09/837,720 filed Apr. 18, 2001 now U.S. Pat. No. 6,655,385 which is a continuation of patent application Ser. No. 09/184,111 filed Nov. 2, 1998 now U.S. Pat. No. 6,439,234 which is a continuation of International Application PCT/US98/05573 filed Apr. 3, 1998 which claims the benefit of provisional patent application Ser. No. 60/045,080 filed Apr. 29, 1997.

FIELD OF THE INVENTION

The present invention relates to a cannula which is provided with a pair of nares which each have a primary aperture or opening formed in an end surface or wall thereof defining a primary flow path into and out of the nare for supplying a desired gas to a nostril of a patient, withdrawing or sampling a desired gas from a nostril of a patient (e.g., sampling end tidal $CO_2$ in the exhaled gases of a patient), monitoring breathing characteristics of a patient (such as respiratory air waves and air flow), detecting changes in pressure within the nostril as the patient breathing, etc., and is further provided with at least one additional secondary opening(s), within at least one and preferably both of the nares, for providing a secondary flow passage into and out of the nare for supplying a desired gas to a nostril of a patient, withdrawing a desired gas from a nostril of a patient (e.g., sampling end tidal $CO_2$ in the exhaled gases of a patient), monitoring breathing characteristics of a patient (such as respiratory airwaves and airflow), or detecting changes in pressure as the patient breathing, etc., in the event that the primary breathing path becomes occluded, blocked, clogged or otherwise either partially or fully obstructed.

BACKGROUND OF THE INVENTION

The practice of measuring end-tidal carbon dioxide during the administration of anesthesia, particularly regional anesthesia, has grown markedly in the past several years. The reasons that anaesthesiologists have embraced this technique are described more fully in U.S. Pat. No. 5,335,656 which is incorporated herein by reference in its entirety.

The preferred nasal cannula used in this procedure is a cannula which insufflates the patient with oxygen through one nare of a cannula and separately samples the exhaled gases by drawing the exhaled gas from the other nare into a conventional carbon dioxide analyzer. The cannula is preferably provided with an internal wall, a partition, a barrier or a system in the face piece to keep the conduits completely separate from one another for insufflation and sampling, however, separate lines can be used or even multiple nares for insufflation and sampling, though the latter device substantially increases the risk of gases mixing which can distort the readings for end-tidal carbon dioxide. It is preferred that two nares only are employed and that each nare performs only one function, i.e., insufflation or sampling into or from separate nostrils, detecting pressure or breathing characteristics, etc. Likewise, insufflation has normally been continuous, however, it could advantageously be intermittent which would further improve the end-tidal carbon dioxide measurement by insuring that gases being sampled where representative of exhaled gases undiluted by the other gases being insufflated. Most preferably, the intermittent insufflation is accomplished by the apparatus and method described in U.S. Pat. No. 5,626,131 which is incorporated herein by reference in its entirety. Other so-called demand insufflation devices which being insufflation upon the start of inhalation can also be employed.

Normal nasal cannulae are designed with the nares having a slight inward curvature as the nares extend upward from the face piece. This is anatomically desirable and important for imparting the proper direction of the insufflating gas into the nasal cavities, receiving the sampled gas(es) from the patient, detecting pressure or breathing characteristics of the patient, etc. When the patient is in the upright sitting position or ambulatory, this is the most satisfactory design configuration. Conversely, problems can be encountered if the patient is horizontal or prone and tends to accumulate secretions in the nasal cavities. It can be a particularly vexing problem if either the insufflation or sampling nare becomes occluded during the use of the cannula for sampling, monitoring end-tidal carbon dioxide during the administration of anesthesia, detecting pressure or breathing characteristics of a patient, etc.

One problem which can readily occur during use of a cannular positioned in the nostrils of a patient is that the primary opening, formed in the remote end wall or surface, of one or both of the nares may become either partially or fully occluded, blocked, clogged or otherwise obstructed by, for example, mucosal secretions and/or soft mucosal tissue during use of the nasal cannula. This is particularly true if the nasal cannula is used in a patient for an extended period of time, e.g., for a few hours to eight or more hours during a sleep diagnostic session. Over the course of time, the mucosal secretions and/or soft mucosal tissue, as well as any inhaled particulate matter which may collect within the nostrils, can either partially or completely occlude, block, clog or otherwise obstruct the primary inlet/outlet opening to one or both nares and such occlusion, blockage, or obstruction can then prevent that nare from properly achieving its intended function, e.g., prevent or seriously inhibit the nare from properly supplying the desired gas to the nostril of the patient, withdrawing or sampling the desired sample from the nostril (e.g., sampling end tidal $CO_2$ in the exhaled gases of a patient), monitoring breathing characteristics of a patient (such as respiratory air waves and air flow), or detecting changes in pressure within the nostril during patient breathing.

OBJECTS OF THE INVENTION

It is, therefore, an object of the present invention to provide a nasal cannula structure for sampling carbon dioxide which reduces or eliminates the incidence of occlusion of the tip of the carbon dioxide sampling nare during the removal of carbon dioxide by the sampling line connected to a monitoring device and/or a source of suction or vacuum.

It is also an object of the present invention to provide a nasal cannula for insufflating a patient with oxygen while accurately monitoring end-tidal carbon dioxide, that will continue to function properly for its intended purpose when either or both nares become occluded for any reason.

It is a further object to accomplish the foregoing objects with a minimum risk of distorting the end-tidal carbon dioxide readings from the sampled exhalation gases during the administration of anesthesia.

Still another object of the present invention is to provide at least one, and preferably a pair of opposed openings, in a side wall of the nare, which form a secondary flow path into and out of the nare and insures proper function of the nare in the event that the primary flow path becomes either partially or fully occluded, blocked, clogged or otherwise obstructed by, for example, mucosal secretions, soft mucosal tissue during use of the nasal cannula, any inhaled particulate matter which may collect within the nostrils, etc. That is, the secondary flow path insures that the nare is still able to function properly, e.g., supply a desired gas to the nostril of the patient or withdraw or sample a desired sample from the nostril (e.g., sampling end tidal $CO_2$ in the exhaled gases of a patient), monitoring breathing characteristics of a patient (such as respiratory air waves and air flow), or detect changes in pressure within the nostril during patient breathing, etc., in the event that the primary flow path becomes either partially or fully occluded, blocked, clogged or otherwise obstructed for some reason.

Yet another object of the present invention is to provide both of the nares with at least one, and preferably a pair of opposed openings, in a side walls thereof which form secondary flow paths for each nare and insures proper function of each nare in the event that the primary flow path of that nare becomes either partially or fully occluded, blocked, clogged or otherwise obstructed by, for example, mucosal secretions, soft mucosal tissue during use of the nasal cannula, any inhaled particulate matter which may collect within the nostrils, etc.

Another object of the present invention is to provide the nasal cannula with at least one mouthpiece, and possibly a pair of joined or completely separate mouthpieces, for communicating with a mouth of a patient so that the breathing characteristics (such as respiratory air waves and air flow) may be monitored during a sleep diagnostic session regardless of whether the patient solely breathes through his or her nose, the patient solely breathes through his or her mouth, or alternate breathing between his or her nose and mouth during the sleep diagnostic session. The mouthpiece has an internal fluid passageway which communicates, at one end thereof, with an inlet/outlet aperture or opening formed in end surface of the mouthpiece while an opposite end thereof communicates with an internal chamber or compartment of the nasal cannula.

BRIEF SUMMARY OF THE INVENTION

The foregoing objects and advantages are obtained by providing a nasal cannula structure that is adapted for insufflation and sampling, with additional or secondary holes or vents on or in the nares of the nasal cannula, preferably both anterior and posterior of one or both nares at the location proximate the entrance of the nasal passageways when the cannula is in use for supplying the desired gas to the nostril of the patient or withdrawing or sampling a desired gas sample from the nostril (e.g., sampling end tidal $CO_2$ in the exhaled gases of a patient), or monitoring breathing characteristics of a patient (such as respiratory airwaves and air flow), or detecting changes in pressure within the nostril during patient breathing, etc.

The present invention relates to a nasal cannula for coupling to flow/pressure detection equipment to facilitate collection of respiratory air waves and respiratory air flow of a patient, during a sleep diagnostic session, for inputting to conventional polysomnography equipment and subsequent analysis by sleep lab personnel. The collected data is useful in treating a patient for sleep apnea or a number of other different sleep disorders.

The present invention also relates to a method of monitoring breathing of a patient with a nasal cannula, the method comprising the steps of: forming the nasal cannula with at least one nare, and the at least one nare having a primary inlet/outlet opening formed in a remote end thereof; coupling the nasal cannula to a detection device for monitoring breathing characteristics of the patient while the patient is sleeping; detecting breathing characteristics of the patient, while the patient is sleeping, via at least the primary inlet/outlet opening of the nare; and sending the detected breathing characteristics of the patient to detection device for evaluation.

The present invention also relates to A nasal cannula for monitoring breathing of a patient, the nasal cannula comprising an elongated hollow body for positioning adjacent a nose of the patient; a first nare having a fixed length, a remote free first end of the first nare having a primary inlet/outlet opening therein and being sized to be received within a first nasal passage of the nose, a second end of the first nare being connected to an internal compartment, and the first nare has at least one secondary inlet/outlet opening which communicates with the internal compartment; a second nare having a fixed length, a remote free first end of the second nare having a primary inlet/outlet opening therein and being sized to be received within a second nasal passage of the nose, a second end of the second nare being connected to an internal compartment, and the second nare has at least one secondary inlet/outlet opening which communicates with the internal compartment; and coupling the nasal cannula to a detection device for monitoring breathing characteristics of a patient while the patient is sleeping; detecting breathing characteristics of the patient, while the patient is sleeping, via at least the primary inlet/outlet opening of at least one of the first and second nares; and detecting the breathing characteristics of the patient, via at least the second inlet/outlet opening of at least one of the first and second nares, in the event that the primary inlet/outlet opening of one of the first and second nare becomes at least partially occluded.

DETAILED DESCRIPTION OF THE ILLUSTRATED EMBODIMENT

FIG. 1 is a frontal view of a normally positioned nasal cannula on a patient (shown in phantom) connected to a gas source (G) and a gas analyzer (A);

FIG. 2 is a rear view of the cannulae face piece shown in FIG. 1;

FIG. 3 is a partial cross section of a nare of the nasal cannula taken along the lines and arrows 3-3 of FIG. 2;

FIG. 4 is a top plan view of the nasal cannula of FIG. 2;

Figure 14:
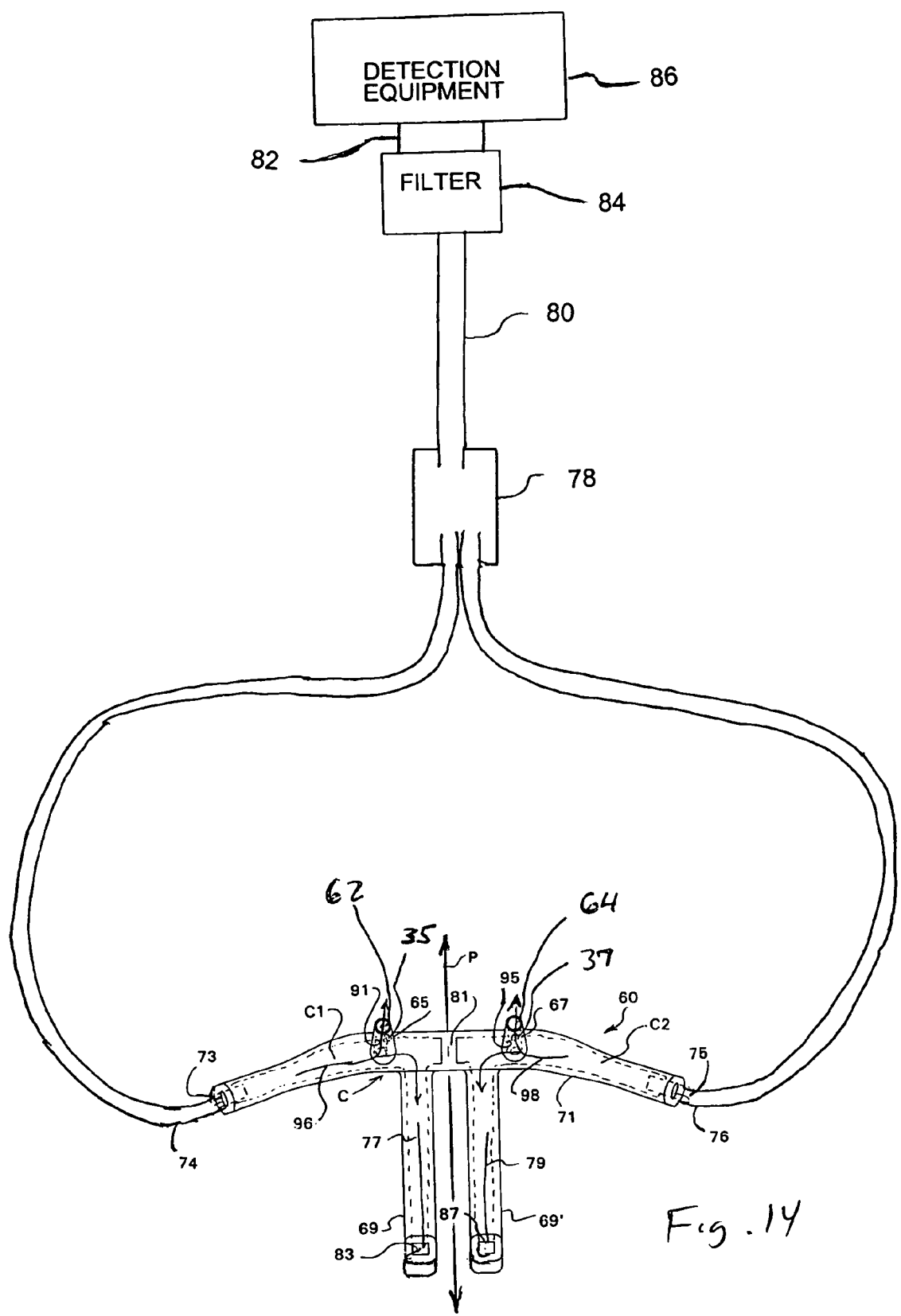
Figure 15:
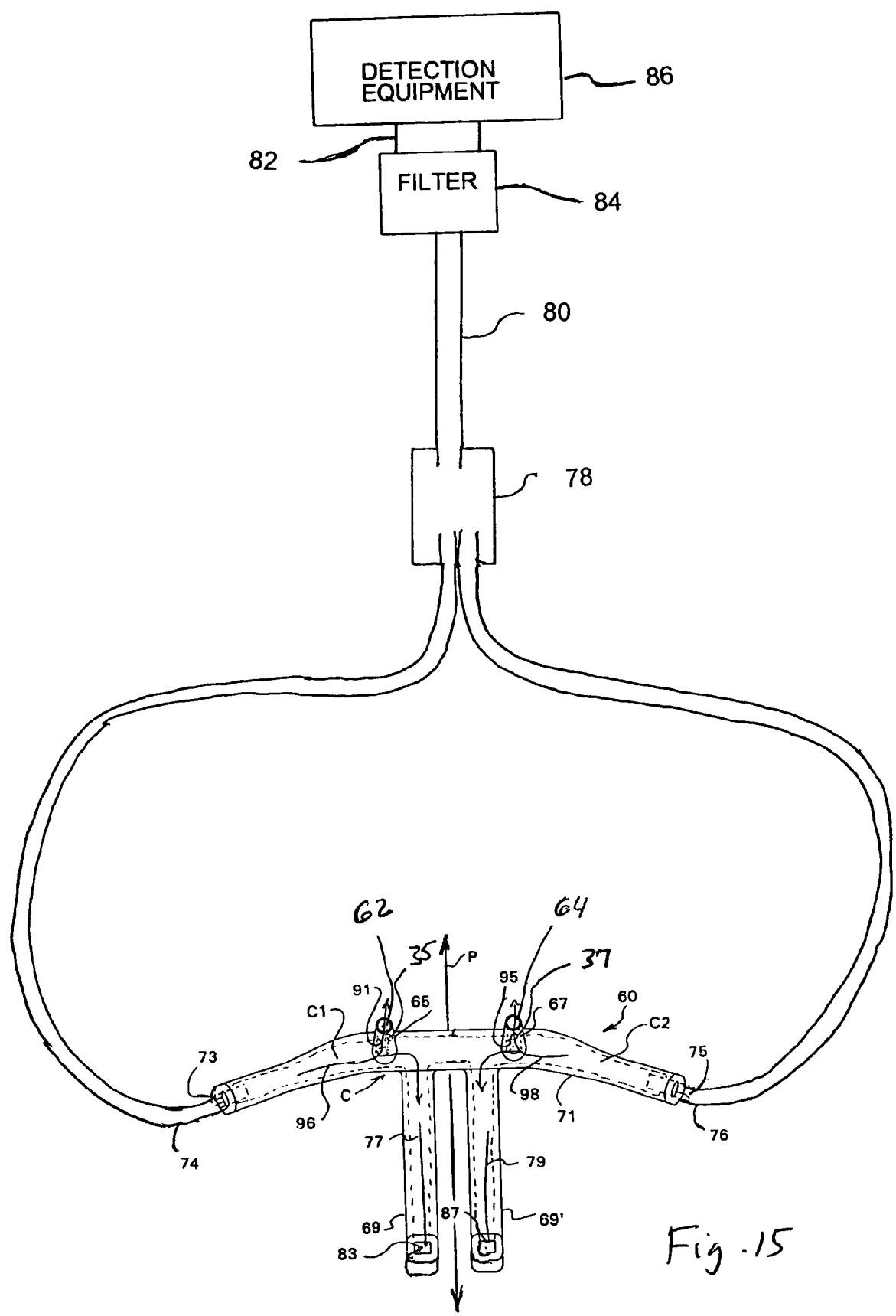

FIG. 14 is a diagrammatic view of a divided nasal cannula, with a pair of separate, spaced apart mouthpieces and with nares having secondary openings therein, for connection to detection equipment to facilitate monitoring of breathing characteristics of a patient; and FIG. 15 is a diagrammatic view of an undivided nasal cannula, with a pair of separate, spaced apart mouthpieces and with nares having secondary openings therein, for connection to detection equipment to facilitate monitoring of breathing characteristics of a patient.

DETAILED DESCRIPTION OF THE ILLUSTRATED EMBODIMENT

The nasal cannula 10 of one embodiment of the present invention comprises or consists of a generally tubular face piece 12 having two spaced apart nares 13 and 14 and an internal septum 15 disposed in the center of the face piece 12 between the flow passage openings 16 and 17, respectively, of the nares 13 and 14 (see FIGS. 2, 3 and 4). The flow passage openings 21 and 22 on the ends of the face piece 12 are affixed to separate conduits or tubes 23 and 24 as shown in FIG. 1, which are separately connected to a source of insufflating gas (G), such as oxygen, and a commercial carbon dioxide monitoring unit (A) which, in turn, has or is connected to a vacuum pump or other means for drawing an exhaled breath, containing carbon dioxide, into an instrument that is capable of measuring the concentration of the carbon dioxide in the sampled gas.

During use of the cannula for both insufflation and the monitoring of carbon dioxide concentration in the exhaled breath (depicted schematically in FIG. 1), the readings for end-tidal carbon dioxide can become distorted when there is undesirable mixing with room air or with excess insufflating gas. Likewise, carbon dioxide measuring devices which typically employ varying amounts of suction or vacuum to obtain the gas sample to be analyzed, can unduly dilute the sample or more seriously can draw the inlet/outlet opening 31, located in the tip 30 of the sampling nare (representatively shown in FIG. 3), into contact with the adjacent surface of the tissue of the nasal passage and either partially or fully occlude the inlet/outlet opening 31 thereby restricting or even preventing sampling of the exhaled gases for their carbon dioxide concentration.

This is an especially serious problem where the patient is prone to generate secretions and the secretions are present so as to be drawn into the inlet/outlet opening 31 at the tip 30 and then either partially or fully occlude, block, clog or otherwise obstruct the opening 31, during the administration of anesthesia or a sleep diagnostic session, for example.

The anesthesiologist must respond by clearing the nare opening after first removing the cannula from its initially installed location on the face of the patient. This may be complicated especially where the patient is draped in a manner which covers the cannula, such as in eye surgery. It may also be difficult to detect the occlusion where the end-tidal carbon dioxide measurement signal is only partially, but not fully, degraded.

It has been discovered that the expedient of additionally providing the nares with very small holes or openings, shown collectively at 35, 36, 37 and 38 adjacent the tip 30, achieves the desired result of preventing an undesirable and unnecessary level of suction at the opening 31 of the tip 30 from developing sufficiently to draw the opening 31 into the nasal tissue thereby either partially or fully occluding, blocking, clogging or otherwise obstructing the opening 31. The holes are sized large enough to prevent sufficient suction from developing at the tip 30 so as to draw in mucosal secretions or attach the tip by suction to the soft mucosal tissue, while still facilitating drawing an undiluted sample of the exhaled gases to provide good end-tidal carbon dioxide measurements. Likewise, too large an opening for these holes would undesirably dilute the exhaled gas sample with room air or excess insufflation gas.

The openings 35, 36, 37 and/or 38 also facilitate obtaining or withdrawing a desired sample from the nostril (e.g., sampling end tidal $CO_2$ in the exhaled gases of a patient), monitoring breathing characteristics of a patient (such as respiratory air waves and air flow), or detect changes in pressure within the nostril during patient breathing, etc., by providing a secondary flow path in the event that the primary flow path becomes either partially or fully occluded, blocked, clogged or otherwise obstructed during use of the cannula.

As previously noted, the nasal cannula of the present invention can be used in combination with an oxygen delivery system that delivers the insufflating gas intermittently. The delivery can be initiated at any time after the peak end-tidal carbon dioxide measurement is achieved during exhalation and continuing into the inhalation phase of the breathing cycle or could be inhalation activated or designed to deliver only during selected portions of all or only some of the inhalation phases of a patient's breathing cycles. Preferably, the delivery should begin before the termination of the exhalation phase, such as is described in U.S. Pat. No. 5,626,131. Using intermittent delivery substantially reduces the possibility of distorted carbon dioxide readings due to gas mixing.

Likewise, slits or slots (not shown) may be employed in the nares which could function in the same manner as the holes describe if they are positioned in such a manner to avoid collapse or occlusion with the nasal tissues and provide the desired function of preventing sufficient suction from developing at the tip of the nare to cause it to be drawn, by suction, onto the tissues. The holes provided as described herein are preferred as there is less risk of occlusion and trauma from the edges of slits or slots to the nasal tissue and potentially there is less risk of occlusion and trauma from the edges of slits or slots to the nasal tissue and potentially there is less risk of gas dilution and mixing from occurring where the slits or slots are overly large.

Further, the combination of intermittent insufflation using the cannula of the present invention produces the desired end-tidal carbon dioxide measurement, as described, and helps prevent patient desaturation during the rigors of surgery and anesthesia administration.

Preferably, the size of the openings from between about 0.05 to about 0.07 of an inch or so though larger or smaller holes or a single hole may be advantageously employed in combination with specific analytical apparatuses. The size and location of the openings can vary with the analyzer selected and the proper function confirmed without undue experimentation.

It is to be appreciated that as discussed above, the cannula may have only a single hollow nasal prong or nare, a pair of nasal prongs or nares and the cannula can be divided or undivided. In addition, the spacing from the nare will vary depending upon whether the cannula is used for neonatal, pediatric or an adult. In addition, the spacing of the mouthpieces, if more than one mouthpiece is utilized, can vary from application from application. The important aspect of the present invention is that the secondary inlet/outlet openings are provided in the nare to allow the nare to function even if the primary inlet/outlet becomes substantially blocked, clogged, obstructed or occluded for one reason or another. The secondary holes allow the nare to still operate and preform the intended function. That is, the secondary inlet/outlet opening(s) still allow the nare to supply a treating gas to the nostril of the patient, allow sampling or withdrawal of an exit gas being exhausted by the nostril of the patient (e.g., sampling end tidal $CO_2$ in the exhaled gases of a patient), allow monitoring or detection of the breathing characteristic via the nare, etc.

The inventors of the present invention have found that the secondary inlet/outlet opening(s), provided in at least one of the nares, is very useful in monitoring breathing characteristics of a patient (e.g., detecting changes in pressure during breathing), to sleep lab personnel, in the event that one or both of the primary inlet/outlet openings of the nares becomes either partially or fully occluded, blocked, clogged or otherwise obstructed by, for example, mucosal secretions, soft mucosal tissue during use of the nasal cannula, any inhaled particulate matter which may collect within the nostrils, etc.

The inventors have determined that the primary inlet/outlet opening in combination with the secondary inlet/outlet opening(s) ensure the ability of the nare to adequately detect or sense the change in pressure within the nasal cavity of the patient, wearing the nasal cannula, as the patient breathes while he or she is sleeping and being monitored. In addition, the secondary inlet/outlet opening is still able to adequately detect or sense the change in pressure within the nasal cavity of the patient, wearing the nasal cannula, as the patient breathes while he or she is sleeping and being monitored. That is, the secondary inlet/outlet opening is still able to detect changes in pressure, e.g., from negative to positive and vice versa, as the patient discontinues inhalation (negative pressure) and commences exhalation (positive pressure), and vice versa, withdraw or sample a desired gas sample from the nostril (e.g., sampling end tidal $CO_2$ in the exhaled gases of a patient), monitoring breathing characteristics of a patient (such as respiratory air waves and air flow), etc. As a result of this, the sleep diagnostic equipment is still able to continue monitoring the breathing characteristics of the patient, while the patient remains sleeping.

If the nasal cannula were unable to continue to monitor breathing characteristics of the patient, detect pressure, sample a desired gas, etc., the sleep lab technician will generally alter or manipulate the position of the nasal cannula in an attempt to remove or alleviate the occlusion, blockage, clog or obstruction, while the patient is still sleeping, without waking or arousing the patient. In some instances, the sleep lab technician may have to completely remove the nasal cannula, clear the occlusion, blockage, clog or obstruction, and then reinstall the nasal cannula while the patient is still sleeping, without waking the patient. However, if the patient wakes up during such manipulation or removal by the sleep lab technician, this will delay somewhat the sleep lab test or may possibly cause the sleep lab technician to restart patient testing and this can be costly and time consuming. It is to be appreciated that without the additional secondary inlet/outlet opening, provided in a side wall of the nare, in many instances the patient may be sufficiently aroused or awakened, as the sleep lab technician attempts to manipulate or remove the cannula to remove or alleviate the occlusion, blockage, clog or obstruction.

Figure 5:
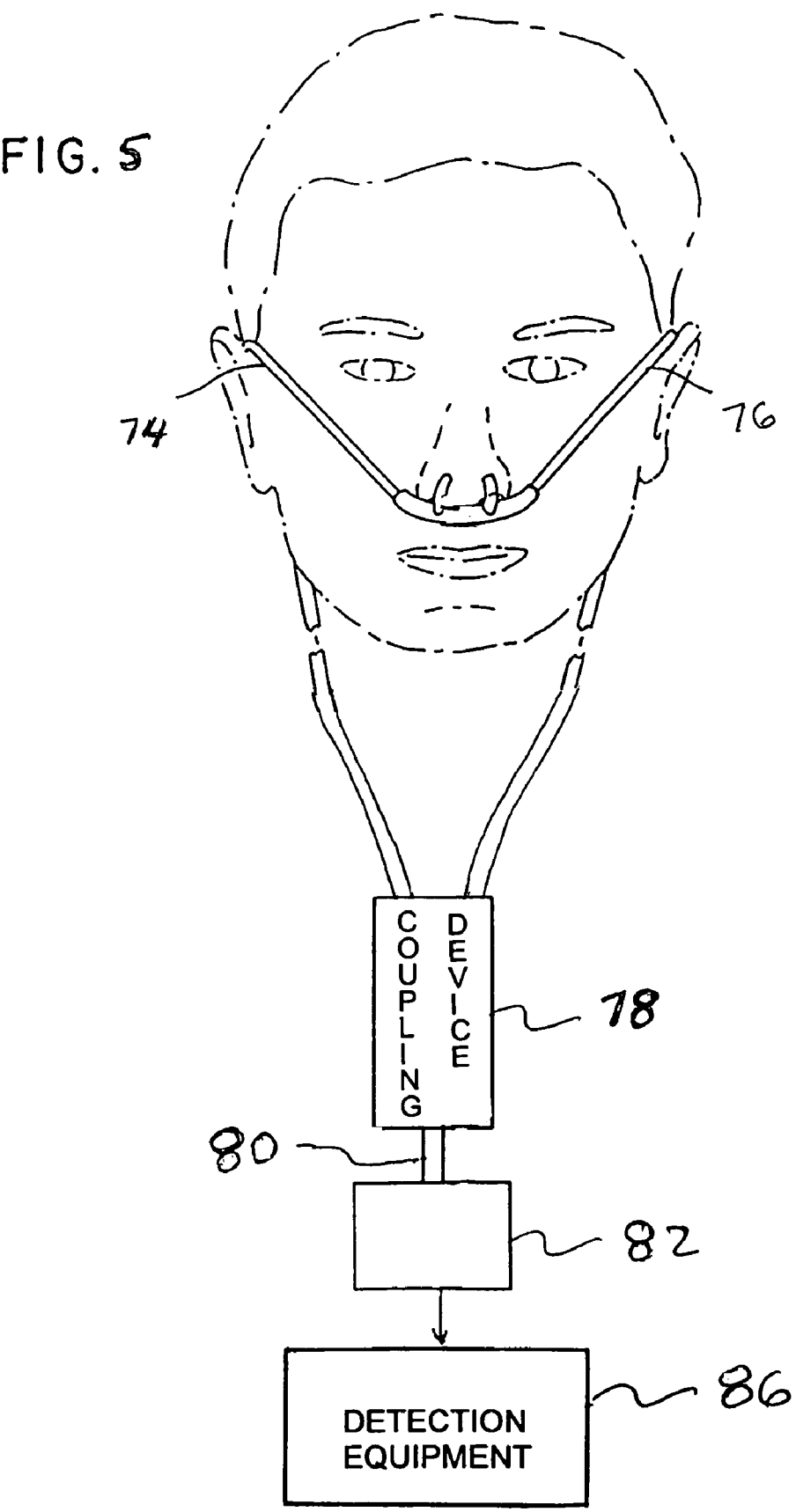
FIG. 5 is a diagrammatic view of a nasal cannula for connection to detection equipment to facilitate monitoring of breathing characteristics of a patient.
Figure 6:
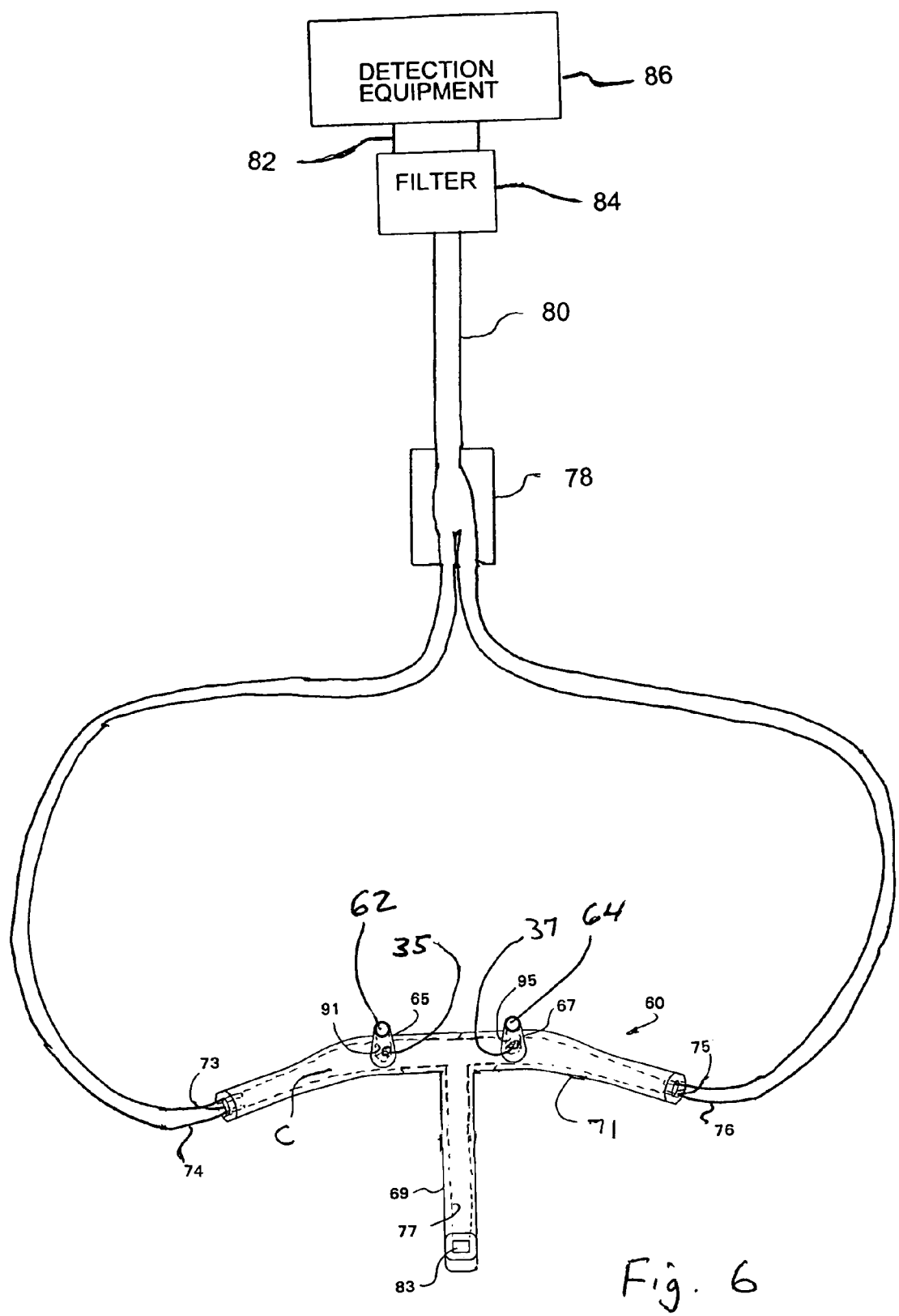
FIG. 6 is a diagrammatic view of a nasal cannula, with a mouthpiece, for connection to detection equipment to facilitate monitoring of breathing characteristics of a patient.

With reference to FIG. 6, another embodiment of the cannula will now be discussed. As this embodiment is very similar to the previous embodiment, identical reference numerals will given to identical elements and only the differences between this embodiment and the previous embodiment will be discussed in detail.

The only significant difference between this embodiment and the previous embodiment is the addition of a curved mouthpiece which is connected to the main body of the cannula for monitoring the breathing characteristics of a patient, obtaining a desired sample, detecting pressure, for example, for a mouth breathing patient. That is, the nasal cannula 60 comprises a single flow path having three separate inlet/outlet openings 62, 64 and 83 to the central internal chamber or compartment C defined by the main body. Each one of the three inlet/outlet openings 62, 64 and 83 to the central internal chamber or compartment C is suitable for monitoring breathing characteristics, detecting pressure, withdrawing or sampling an exhalation gas(es) from the patient nostril (e.g., sampling end tidal $CO_2$ in the exhaled gases of a patient), measuring differential air flow along the tubing connect to the cannula, supplying a treating gas to a patient, etc., both via either a nostril or the mouth of a patient. The central chamber or compartment C of the main body 71 of the cannula 60 is in constant and continuous communication with an inlet/outlet opening 83, formed in the end surface of the mouthpiece 69, via a gas passageway 77 in the mouthpiece 69 and also in constant and continuous communication with the inlet/outlet opening 62, formed in the end surface of the first nare 65, and the secondary inlet/outlet opening(s) 35 and/or 36 via a gas passageway 91 in the first nare 65 and in constant and continuous communication with the inlet/outlet opening 64, formed in the end surface of the second nare 67, and the secondary inlet/outlet opening(s) 37 and/or 38 via a gas passageway 95 in the second nare 67. In addition, the central chamber or compartment C of the main body 71 also communicates with first and second opposed chamber end openings 73, 75 of the cannula 60. As a result of this arrangement, each one of these inlet/outlet openings 62, 64 and 83 can facilitate preforming one of the following functions: monitor breathing of a patient via the mouth and/or the nose, sampling the end tidal $CO_2$ content in the exhaled breath of a patient via the mouth and/or the nose to determine the patient's $CO_2$ concentration level in the blood, measuring differential air flow along the tubing connect to the cannula, supplying a treating gas to a patient via the mouth and/or the nose, detecting changes in pressure air flow, or detecting apnea via the mouth and/or the nose, etc.

A first conduit or tubing 74 is connected to the first end chamber opening 73 while a first end of a second conduit or tubing 76 is connected to a second chamber end opening 75. The opposed second ends of the first and second conduits or tubings 74 and 76 are connected to a coupling device 78 which couples the first and second conduits or tubings 74 and 76 to a common conduit or tubing 80 which is also connected to the coupling device 78. The opposite end of the common conduit or tubing 80 typically has a luer connector 82 which is either coupled to a filter 84, prior to engaging with a pressure detection device or detection equipment 86 or, preferably, the filter 84 may be incorporated into the conventional luer connector 82 and this unitary structure will then facilitate coupling of the nasal cannula 60 to the pressure detection device or detection equipment 86 in a conventional fashion. The first and second conduits or tubings 74 and 76 each have a length of about 8 inches to about a 24 inches or so and preferably have a length of about 15 to 25 inches or so while the common conduit or tubing 80 typically has a length of about 3 feet to about 10 feet, preferably a length of about 5 to 7 feet or so.

Figure 7:
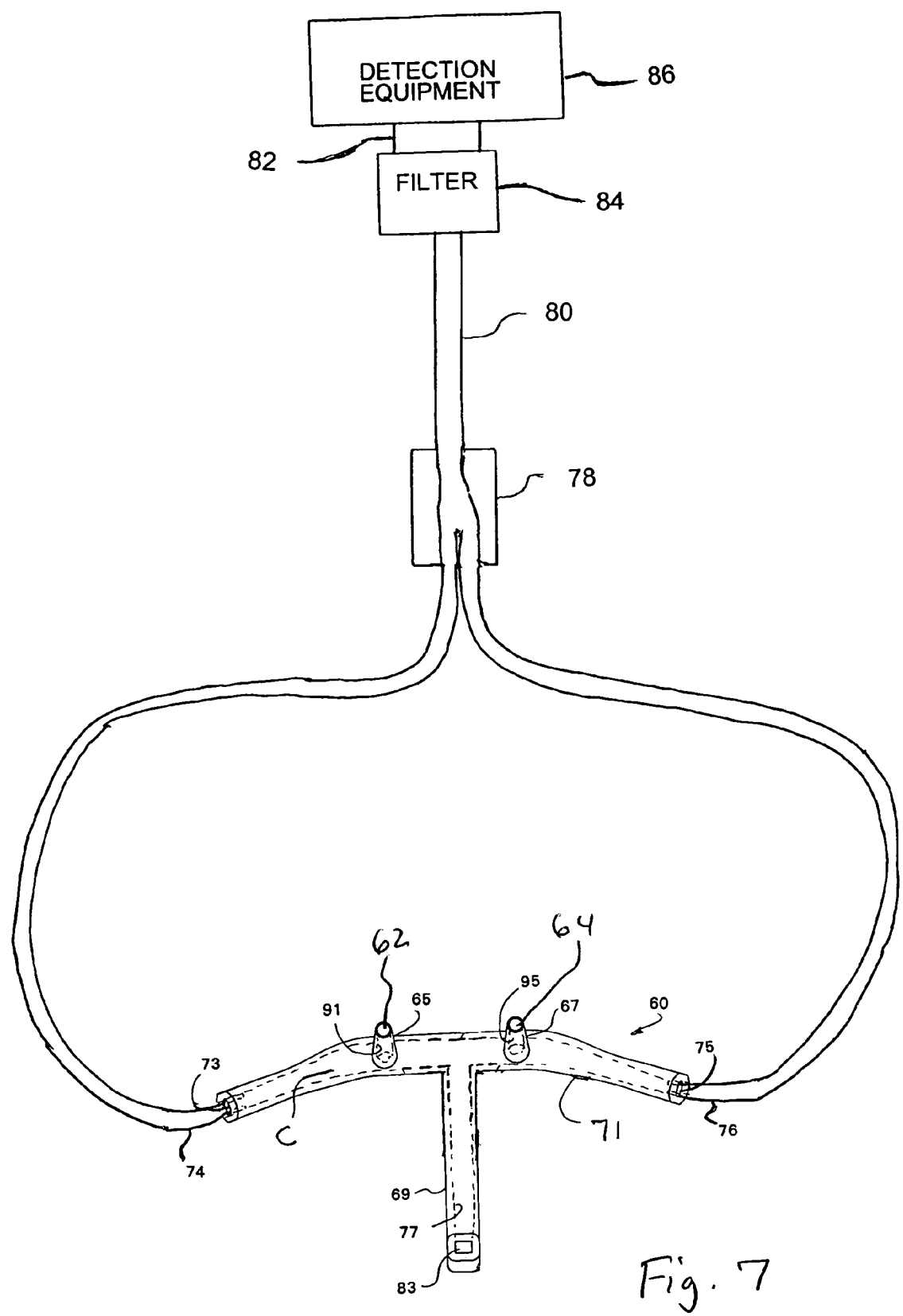
FIG. 7 is a diagrammatic view of a nasal cannula, with a mouthpiece but without any secondary openings in the nares, for connection to detection equipment to facilitate monitoring of breathing characteristics of a patient.

With reference to FIG. 7, another embodiment of the cannula will now be discussed. As this embodiment is very similar to the embodiment of FIG. 7, identical reference numerals will given to identical elements and only the differences between this embodiment and the previous embodiment will be discussed in detail.

The only significant difference between this embodiment and the embodiment of FIG. 7 is the elimination of all of the secondary inlets/outlets openings 35, 36 and 37, 38, adjacent the tip so that each nare 65 and 67 only has a primary flow passage into and out of the nare but not any secondary flow passage in the event that the primary inlets/outlets openings 62, 64 of the nares 65, 67 become either partially or fully occluded, blocked, clogged or otherwise obstructed during use of the nasal cannula. That is, flow into and out of the nares 65, 67 can only occur via the primary inlet/outlet openings 62, 64 formed in the nares 65, 67, respectively.

Figure 8:
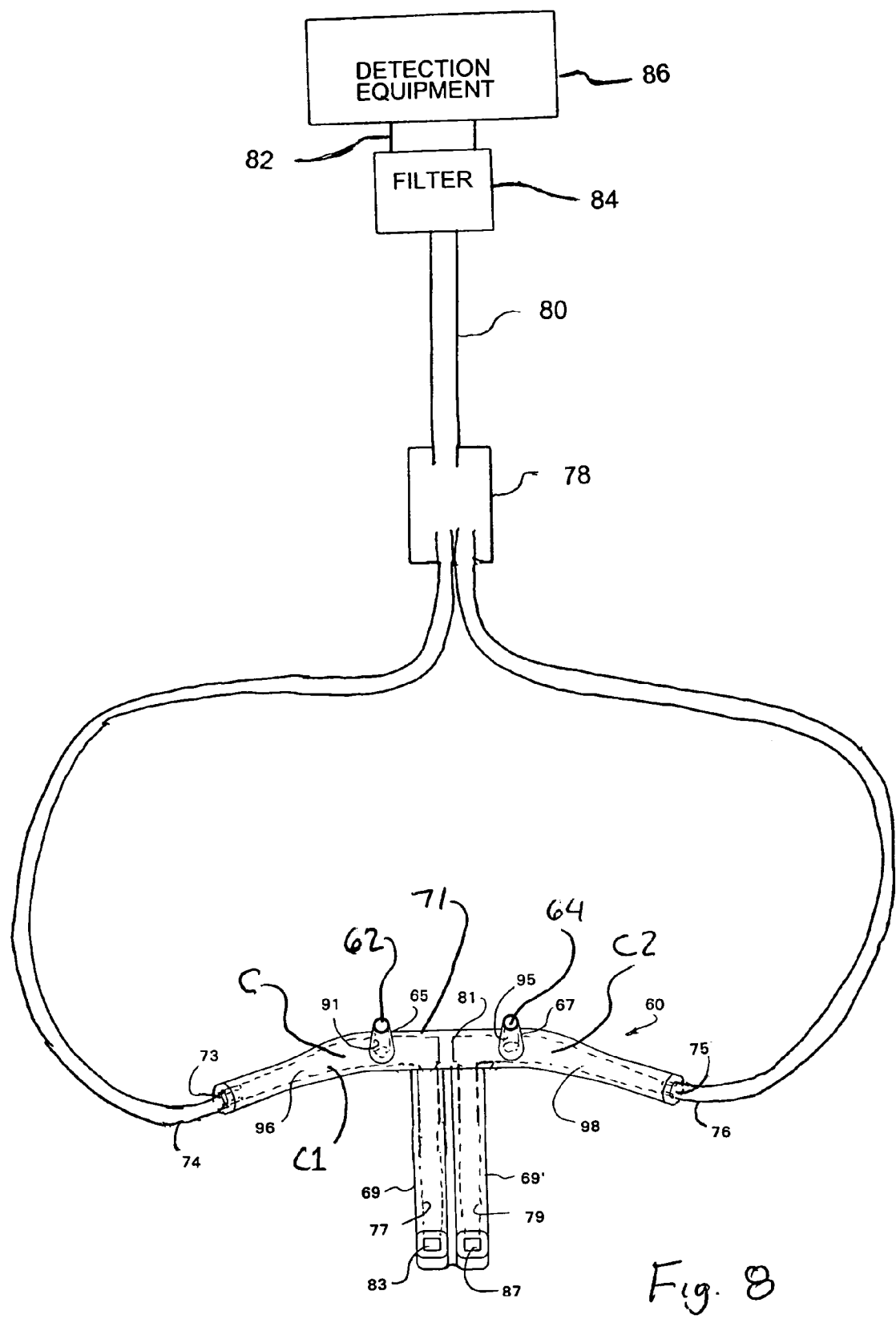
FIG. 8 is a diagrammatic view of a divided nasal cannula, with a pair of integral mouthpieces but without any secondary openings in the nares, for connection to detection equipment to facilitate monitoring of breathing characteristics of a patient.

With reference to FIG. 8, still another embodiment of the cannula will now be discussed. As this embodiment is very similar to the embodiment of FIG. 7, identical reference numerals will given to identical elements and only the differences between this embodiment and the previous embodiment will be discussed in detail.

The only significant differences between this embodiment and the embodiment of FIG. 7 is the inclusion of a second integral mouthpiece 69' and the addition of an internal divider or septum 81, within the internal chamber or compartment C, which divides the internal area of the cannula into two separate chambers or compartments C1 and C2. That is, the nasal cannula 60 comprises two completely separate internal flow paths 96 and 98. Each one of the two completely separate internal flow paths 96 and 98 is suitable for monitoring breathing characteristics, detecting pressure, withdrawing or sampling an exhalation gas(es) from the patient nostril (e.g., sampling end tidal $CO_2$ in the exhaled gases of a patient), measuring differential air flow along the tubing connect to the cannula, supplying a treating gas to a patient, etc., both via a nostril and the mouth of a patient. The first compartment or passageway C1, of the internal chamber C of the main body 71 of the cannula 60, is in constant and continuous communication with an inlet/outlet opening 83, formed in the end surface of the first mouthpiece 69, via a gas passageway 77 in the first mouthpiece 69 and also in constant and continuous communication with the inlet/outlet opening 62, formed in the end surface of the first nare 65, via a gas passageway 91 in the first nare 65 and with the first chamber end opening 73 of the cannula and all of these components and passageways form the first completely separate internal flow path 96.

Figure 9:
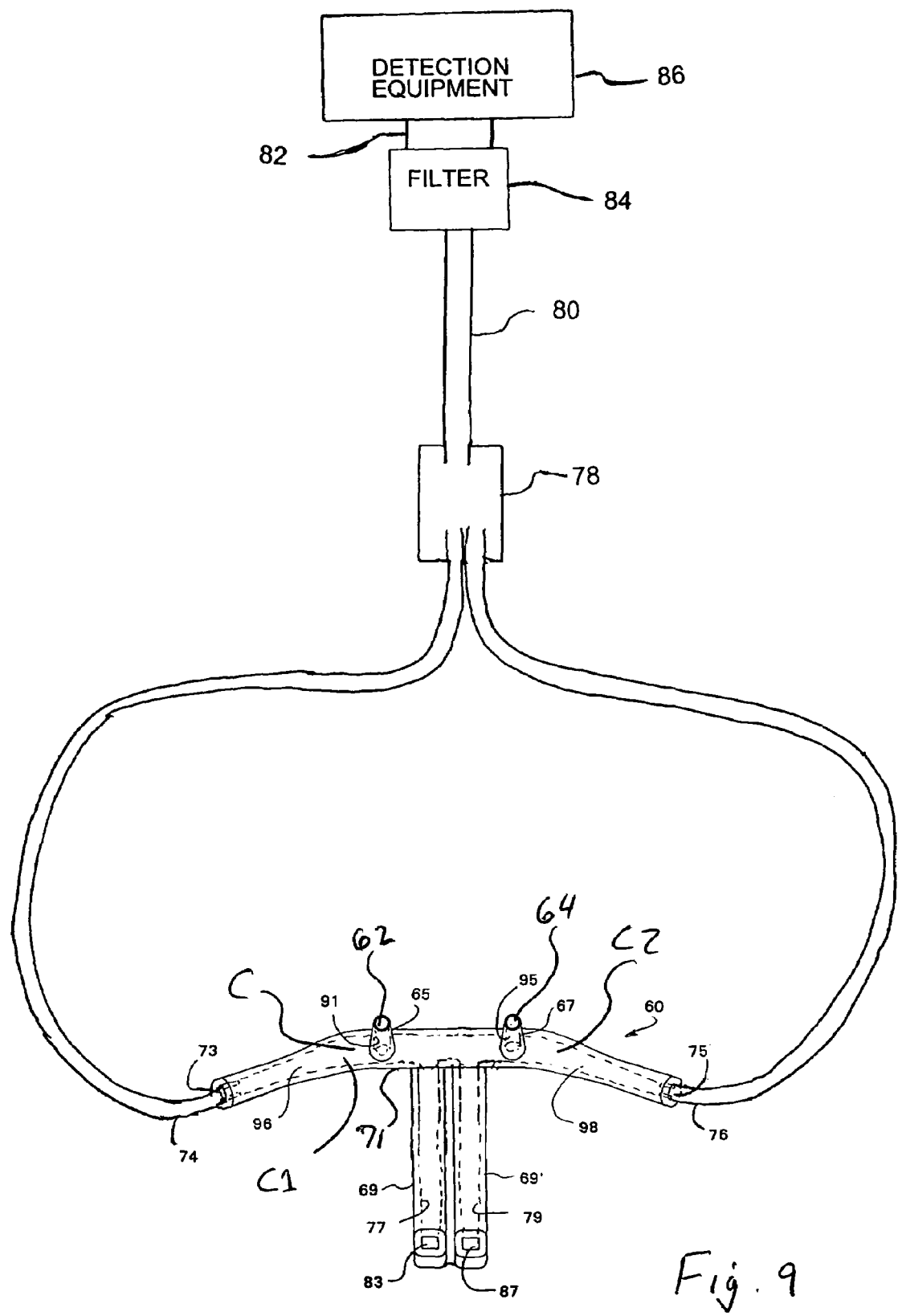
FIG. 9 is a diagrammatic view of an undivided nasal cannula, with a pair of integral mouthpieces but without any secondary openings in the nares, for connection to detection equipment to facilitate monitoring of breathing characteristics of a patient.

The second compartment or passageway C2, of the internal chamber C of the main body 71 of the cannula 60, is in constant and continuous communication with the inlet/outlet opening 87, formed in the end surface of the second mouthpiece 69', via a gas passageway 79 in the second mouthpiece 69' and also in constant and continuous communication with the inlet/outlet opening 64, formed in the end surface of the second nare 67, via a gas passageway 95 in the second nare 67 and with the second chamber end opening 75 of the cannula 60 and all of these components and passageways form the second completely separate internal flow path 98. As a result of these completely separate fluid passageways 96, 98, each completely separate fluid passageway 96 or 98 can facilitate preforming one of the following functions: monitor breathing of a patient via the mouth and/or the nose, sampling the end tidal $CO_2$ content in the exhaled breath of a patient via the mouth and/or the nose to determine the patient's $CO_2$ concentration level in the blood, measuring differential air flow along the tubing connected to the cannula, supplying a treating gas to a patient via the mouth and/or the nose, detecting apnea via the mouth and/or the nose, etc. If desired, the septum 81 may be eliminated (as in FIG. 9) so that the first and second compartments or passageways C1 and C2, the first and second internal gas passageways 77, 79 and the first and second gas passageways 91 and 95 in the nares 65 and 67 and all of the openings 62, 64, 73, 75, 83 and 87, are in constant and continuous communication with one another.

Figure 10:
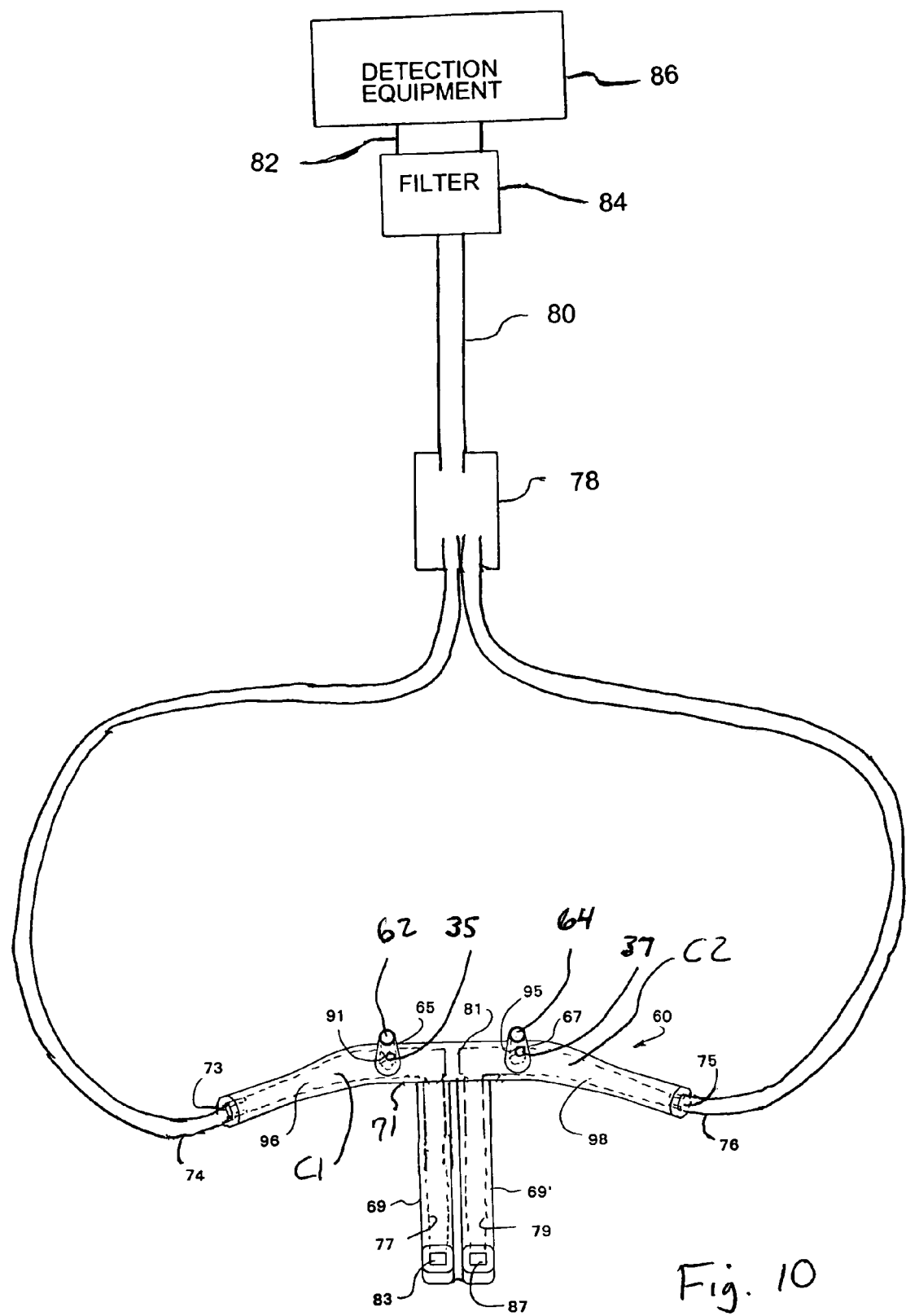
FIG. 10 is a diagrammatic view of a divided nasal cannula, with a pair of mouthpieces and with secondary openings in the nares, for connection to detection equipment to facilitate monitoring of breathing characteristics of a patient.

With reference to FIG. 10, yet another embodiment of the cannula will now be discussed. As this embodiment is very similar to the embodiment of FIG. 8, identical reference numerals will given to identical elements and only the differences between this embodiment and the previous embodiment will be discussed in detail.

The only significant difference between this embodiment and the embodiment of FIG. 8 is the inclusion of at least one, and preferably a pair of secondary inlets/outlets openings 35, 36 and 37, 38, adjacent the tip of each one of the nares 65, 67 to provide a pair of secondary flow passages 96, 98 in the event that the primary inlets/outlets openings 62, 64 of the nares 65, 67, respectively, become either partially or fully occluded, blocked, clogged or otherwise obstructed during use of the nasal cannula 60. The secondary inlets/outlets openings 35, 36 and 37, 38 are smaller than the primary inlet/outlet openings 62, 64 but are large enough to facilitate withdrawing or sampling a desired gas sample from the nostril (e.g., sampling of end tidal $CO_2$ in a patient), monitoring breathing characteristics of a patient (such as respiratory airwaves and air flow), detecting changes in pressure within the nostril, etc., during patient breathing.

Figure 11:
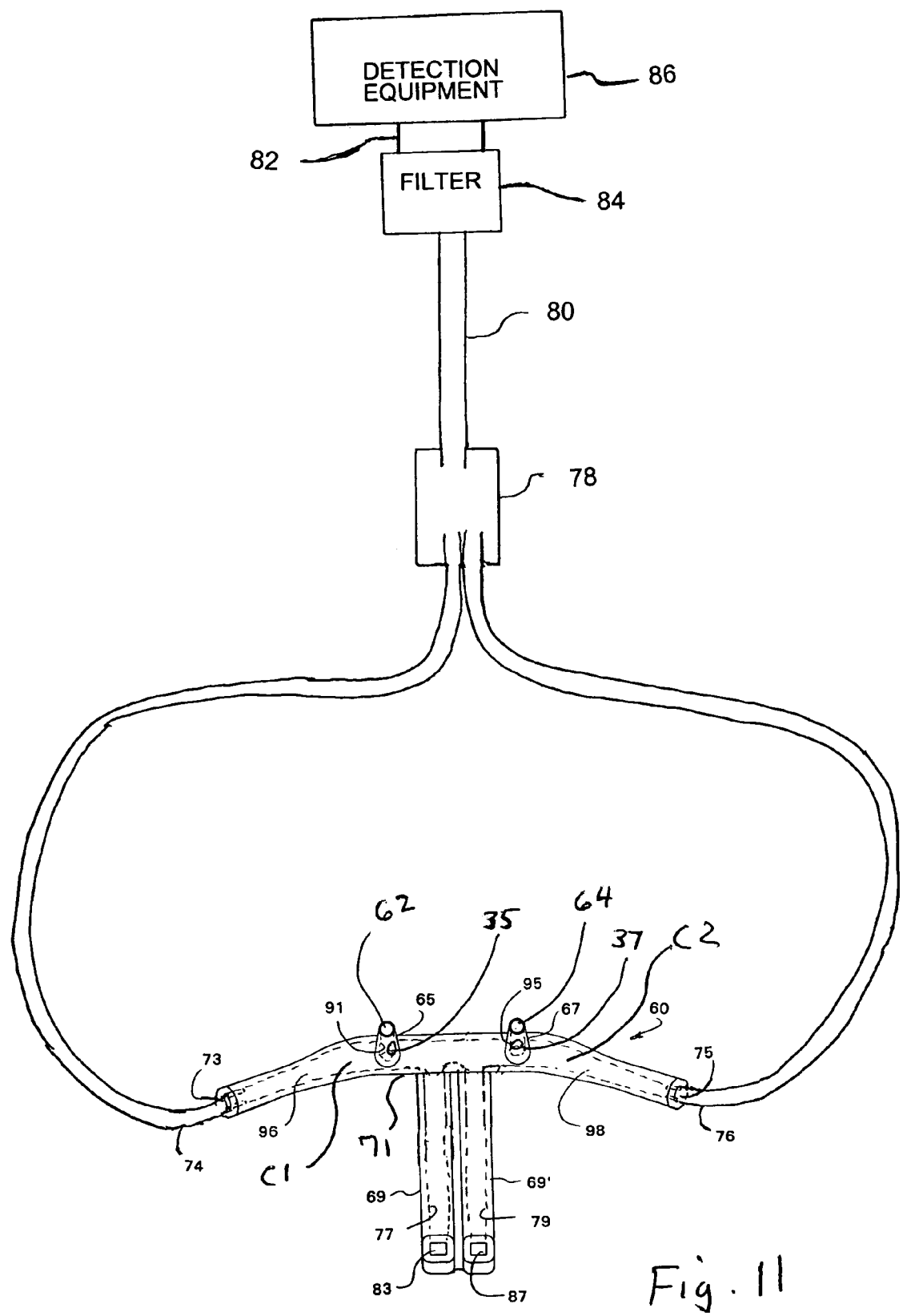
FIG. 11 is a diagrammatic view of an undivided nasal cannula, with a pair of integral mouthpieces and with nares having secondary openings therein, for connection to detection equipment to facilitate monitoring of breathing characteristics of a patient.

With reference to FIG. 11, yet another embodiment of the cannula will now be discussed. As this embodiment is very similar to the embodiment of FIG. 10, identical reference numerals are given to identical elements and only the differences between this embodiment and the previous embodiment will be discussed in detail.

The only significant difference between this embodiment of FIG. 11 and the embodiment of FIG. 10 is that the septum 81 is eliminated so that the first and second compartments or passageways C1 and C2, the first and second internal gas passageways 77, 79 and the first and second gas passageways 91 and 95 in the nares 65 and 67 and all of the openings 35, 36, 37, 38, 62, 64, 73, 75, 83 and 87 are in constant and continuous communication with one another.

Figure 12:
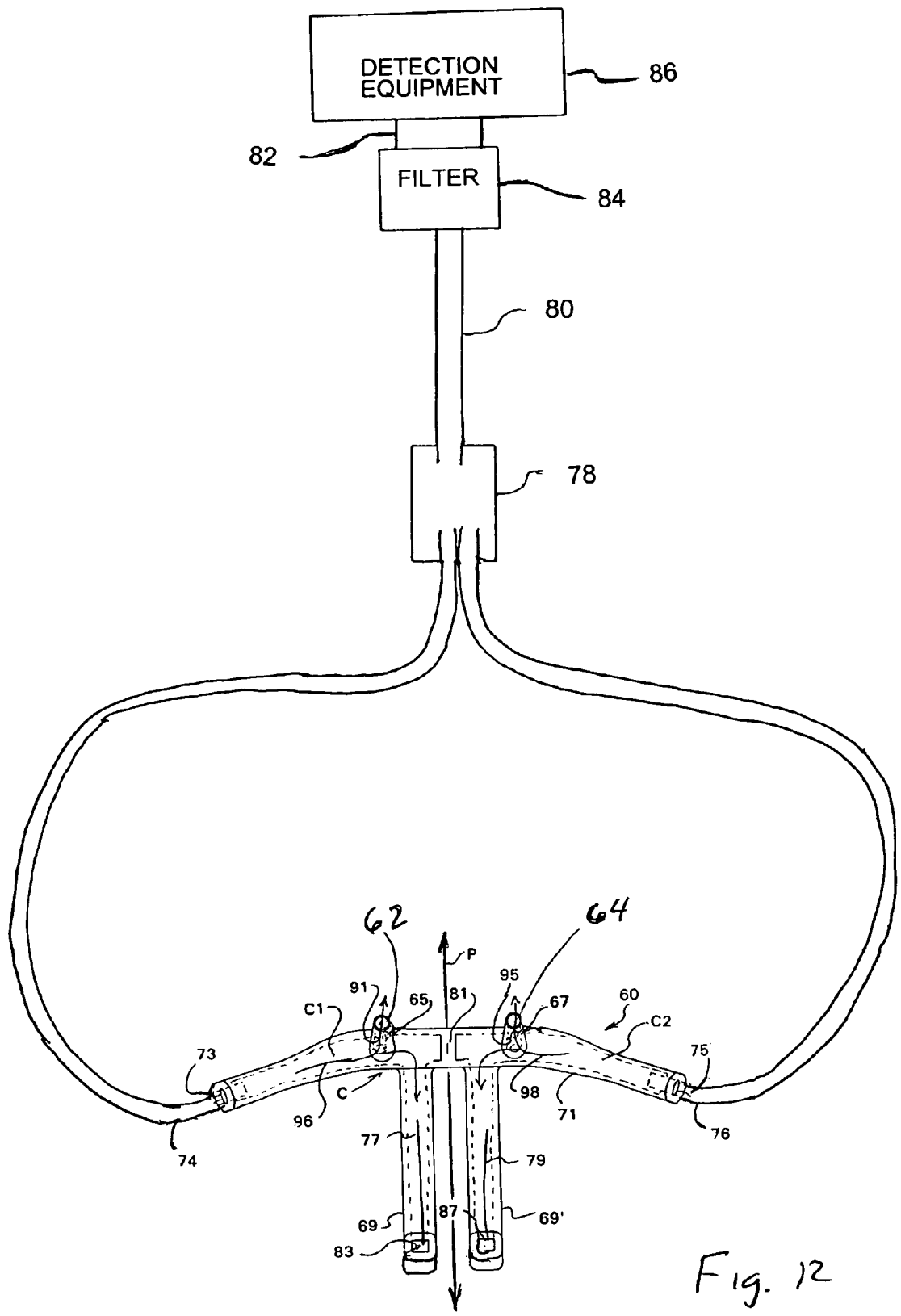
FIG. 12 is a diagrammatic view of a divided nasal cannula, with a pair of separate, spaced apart mouthpieces but without any secondary openings in the nares, for connection to detection equipment to facilitate monitoring of breathing characteristics of a patient.

With respect to the embodiments of FIGS. 8-11, it is to be appreciated that it is not necessary to have the first and second mouthpieces 69, 69' precisely centered between the nares 65, 67. It is possible to position the first and second mouthpieces on one side or the other of a central plane P bisecting a center of main body 71 into two halves. Alternatively, the first and second mouthpieces 69, 69' could be spaced apart from one another and formed as two completely separate and curved mouthpieces (as shown in FIGS. 12-15) with a septum 81 dividing the internal chamber or compartment into two separate internal flow paths 96 and 98 (as shown in FIGS. 12 and 14). Each one of the two completely separate internal flow paths 96 and 98 is suitable for monitoring breathing characteristics, detecting pressure, withdrawing or sampling an exhalation gas(es) from the patient nostril (e.g., sampling end tidal $CO_2$ in the exhaled gases of a patient), supplying a desired gas to the patient, etc.

Figure 13:
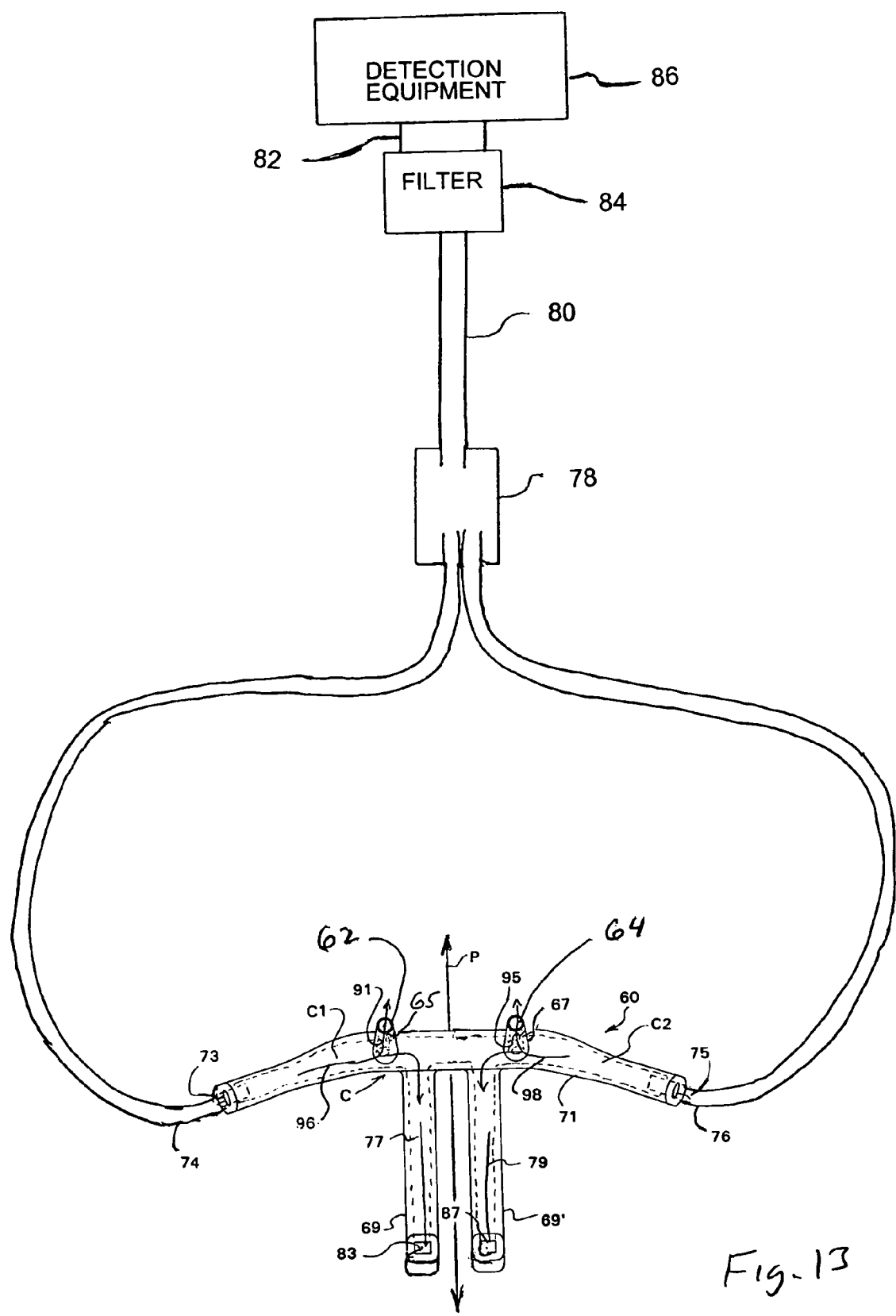
FIG. 13 is a diagrammatic view of an undivided nasal cannula, with a pair of separate, spaced apart mouthpieces but without any secondary openings in the nares, for connection to detection equipment to facilitate monitoring of breathing characteristics of a patient.

In addition, the first and second mouthpieces could be spaced apart from one another, without having a dividing septum 81 therebetween (as shown in FIG. 13), so that both of the nares 65, 67 and both of the first and second mouthpieces 69, 69' all communicate with one another via the common central chamber or compartment formed within the main body 71 of the cannula 60. The spacing of the mouthpieces from one another by a distance of from about 0.25 to about 1.25 inches, and more preferably about 0.5 to about 1.0 inches, is useful if the patient being monitored tends to breath, when mouth breathing, out of one side of his or her mouth. By spacing the mouthpieces from one another, mouthpieces of the nasal cannula are better positioned to still detect or monitor breathing of the patient.

In addition, the first and second nares 65, 67 of FIGS. 12 and 13 may be each provided with at least one, and preferably a pair of secondary inlets/outlets openings, 35, 36 and 37, 38, adjacent the tip 30 of the nares to provide a pair of secondary flow passages 96, 98 (as shown in FIGS. 14 and 15, respectively) in the event that the primary inlets/outlets openings 31 of the nares 65, 67 become either partially or fully occluded, blocked, clogged or otherwise obstructed during use of the nasal cannula. The secondary inlets/outlets openings, 35, 36 and 37, 38 are smaller than the primary inlet/outlet opening but are large enough to facilitate withdrawing or sampling a desired gas sample from the nostril (e.g., sampling of end tidal $CO_2$ in a patient), monitoring breathing characteristics of a patient (such as respiratory air waves and air flow), detecting changes in pressure within the nostril, etc., during patient breathing.

If desired, one or both of the mouthpieces 69, 69' of the cannula 60 can be provided with a shape retaining, dead soft material or wire (not shown) to facilitate alignment and retention of the first and/or second mouthpieces 69, 69' in a desired aligned position during use of the cannula 60. The wire permits the mouthpiece 69 or 69' to be bent, configured or molded into a desired shape, configuration or position while still retaining such desired shape, configuration or position following adjustment of the mouthpiece 69 and/or 69'. A copper wire (either insulated or uninsulated), for example, has substantially no structural memory of any previous shape, orientation, configuration or form which would cause the wire to retain, return or spring back to such previous shape, orientation, configuration or form. Copper is a highly malleable metal and generally retains whatever shape is imparted thereto at any particular time without reverting or returning back to any prior or previous shape. Copper is also a preferred dead soft material, over for example iron, steel or other ferromagnetic materials, due to the propensity of the nasal cannula to be used in connection with a patient exposed to certain electromagnetic and magnetic environments and/or diagnosis procedures.

The wire can either be formed integral with the first and/or second mouthpieces 69, 69', can be accommodated within an integral compartment extending along the length of the first and/or second mouthpieces 69 and/or 69', or can be glued or otherwise permanently secured or affixed to an exterior surface of the first and/or second mouthpieces 69 and/or 69', along the entire length thereof, so that the wire does not become separated or dislodged from the cannula during use of the nasal cannula. The wire typically has a diameter of between 0.01 and 0.2 inches or so.

The first and second mouthpieces 69, 69' each have a radius of curvature of between about 0.5 of an inch to about 2.5 inches or so, and more preferably a radius of curvature of between about 0.75 of an inch to about 1.25 inches or so. The radius of curvature of the mouthpieces 69, 69' can vary, depending upon the cannula being manufactured and/or its application, but is generally chosen to facilitate the alignment of an opening formed in the free end of the mouthpiece 69 and/or 69' with the opening of a mouth of the patient. The first and second mouthpieces 69, 69' each define an internal passageway 77, 79 therein which has a transverse cross sectional flow area of between about 0.006 and about 0.007 square inches.

Since certain changes may be made in the above described improved cannula and method of using the same, without departing from the spirit and scope of the invention herein involved, it is intended that all of the subject matter of the above description or shown in the accompanying drawings shall be interpreted merely as examples illustrating the inventive concept herein and shall not be construed as limiting the invention. That is, the invention described herein is to be limited only by the scope of the appended claims and the applicable prior art.

We claim:

1. A method of monitoring breathing of a patient with a nasal cannula, the method comprising the steps of;

forming the nasal cannula with a hollow body having an internal compartment being divided into a first compartment and a second compartment;

forming a first nare having s fixed length, the first nare being sized to be received within a first nasal passage of a nose of the patient and having a primary inlet/outlet opening formed in a remote end thereof, a second end of the first nare being connected to the first compartment of the nasal cannula and at least one secondary inlet/outlet opening spaced from the primary inlet/outlet opening and communicating with the first compartment;

forming a second nare having a fixed length, the second nare being sized to be received within a second nasal passage of the nose of the patient and having a primary inlet/outlet opening formed in a remote end thereof, a second end of the second nare being connected to the first compartment of the nasal cannula and at least one secondary inlet/outlet opening spaced from the primary inlet/outlet opening and communicating with the second compartment;

forming at least a first mouthpiece connected to the nasal cannula and communicating with the first compartment with a remote end thereof for communicating with a mouth of the patient;

coupling the nasal cannula to a detection device for monitoring breathing characteristics of the patient while the patient is sleeping;

sensing at least one breathing characteristic of the patient, while the patient is sleeping, via at least one of the primary inlet/outlet opening of the first nare and the first mouthpiece; and sensing at least one breathing characteristic of the patient, while the patient is sleeping, via the primary inlet/outlet opening of the second nare;

sending the detected breathing characteristics of the patient to the detection device for evaluation, and in the event that a primary inlet/outlet opening of at least one nare becomes at least partially occluded while the patient is sleeping, detecting the breathing characteristics of the patient via at least the secondary inlet/outlet opening of the partially occluded at least one nare.

2. The method of monitoring breathing of a patient with a nasal cannula according to claim 1, further comprising the step of coupling the nasal cannula to the detection device by first and second tubes; and
providing a filter which at least filters moisture from flowing therealong toward the detection device 3. The method of monitoring breathing of a patient with a nasal cannula according to claim 1, further comprising the steps of providing the nasal cannula with a second mouthpiece separated and spaced apart from the first mouthpiece for communicating with a mouth of the patient and the second mouthpiece communicates with the second compartment and the second nare.

4. The method of monitoring breathing of a patient with a nasal cannula according to claim 3, further comprising the steps of:
preforming a first function using the first compartment and a first flow path; and
preforming a second function using the second compartment and a second flow path.

5. The method of monitoring breathing of a patient with a nasal cannula according to claim 4, further comprising the steps of preforming at least one of the following functions via each of the first and the second flow paths:
a) supplying a treating gas to a nostril of the patient;
b) allow sampling or withdrawal of an exit gas being exhausted by the patient;
c) sampling end tidal $CO_2$ in the exhaled gas of the patient;
d) monitoring or detecting the breathing characteristic of the patient;
e) monitoring and detecting respiratory air waves and air flow of the patient during breathing; and
f) detecting changes in pressure within the nostril during breathing of the patient.

6. The method of monitoring breathing of a patient with a nasal cannula according to claim 1, further comprising the steps of:
preforming a first function using the first compartment and a first flow path; and
preforming a second function using the second compartment and a second flow path.

7. The method of monitoring breathing of a patient with a nasal cannula according to claim 6, further comprising the steps of providing the nasal cannula with a second mouthpiece for communicating with a mouth of the patient, and the second mouthpiece communicates with the second compartment and the second nare.

8. The method of monitoring breathing of a patient with a nasal cannula according to claim 1, further comprising the step of coupling the nasal cannula to a detection device by first and second tubes, and providing a filter for preventing moisture from flowing along the first and the second tubes toward the detection device.

9. A nasal cannula for monitoring breathing of a patient, the nasal cannula comprising an elongated hollow body for positioning adjacent a nose of the patient;
the hollow body having an internal compartment being divided into separate first and second compartments;
a first nare having a fixed length,
a remote free first end of the first nare having a primary inlet/outlet opening therein and being sized to be received within a first nasal passage of the nose,
a second end of the first nare being connected to the first compartment of the nasal cannula, and
the first nare having at least one secondary inlet/outlet opening spaced from the primary inlet/outlet opening and communicating with the first compartment;
a second nare having a fixed length,
a remote free first end of the second nare having a primary inlet/outlet opening therein and being sized to be received within a second nasal passage of the nose,
a second end of the second nare being connected to the second compartment of the nasal cannula,
the second nare having at least one secondary inlet/outlet opening spaced from the primary inlet/outlet opening and communicating with the second compartment; and
at least a first mouthpiece being connected to the nasal cannula and communicating with the first compartment and a mouth of the patient, whereby a detection device, coupled to both the first and the second compartments of the nasal cannula is able to monitor breathing characteristics of a patient while the patient is sleeping through at least one of the primary and secondary inlet/outlet openings of the first nare, and through at least one of the primary and the secondary inlet/outlet openings of the second nare, in an event that the patient is nose breathing, or through the first mouthpiece in an event that the patient is mouth breathing, and
in the event that a primary inlet/outlet opening of at least one of the first and second nares becomes at least partially occluded while the patient is sleeping, at least the secondary inlet/outlet opening of the partially occluded nare facilitates detection of the breathing characteristics of the patient.

10. The nasal cannula for monitoring breathing of a patient according to claim 9, further comprising a second mouthpiece, separated and spaced apart from the first mouthpiece, which communicates with the mouth of the patient and with the second compartment of the nasal cannula.

11. The nasal cannula for monitoring breathing of a patient according to claim 9, wherein:
the first and second compartments of the nasal cannula respectively define first and second flow paths, and
the first flow path includes the primary and secondary inlet/outlet openings of the first nare communicating with first compartment, and
the second flow path includes the primary and secondary inlet/outlet openings of the second nare communicating with second compartment, whereby
a first function can be performed through the first compartment and the first flow path; and
a second function, different from the first function, can be performed through the second compartment and the second flow path.

12. The nasal cannula for monitoring breathing of a patient according to claim 11, wherein:
a second mouthpiece communicates with the primary and secondary inlet/outlet openings of the second nare and with the second compartment.

13. The nasal cannula for monitoring breathing of a patient according to claim 11, wherein the first and the second functions each comprise one of the following:
a) sampling or withdrawing an exit gas being exhausted by the patient;
b) sampling end tidal $CO_2$ in the exhaled gas of the patient;
c) monitoring or detecting the breathing characteristic of the patient;
d) monitoring or detecting respiratory air waves and air flow of the patient during breathing; and e) detecting changes in pressure within the nostril during breathing of the patient.

14. A nasal cannula for monitoring breathing of a patient, the nasal cannula comprising an elongated hollow body for positioning adjacent a nose of the patient;
   the hollow body having an internal compartment being divided into first and second separate compartments;
   a first nare having a fixed length,
      a remote free first end of the first nare having a primary inlet/outlet opening therein and being sized to be received within a first nasal passage of the nose, and
      a second end of the first nare being connected to the first compartment of the nasal cannula;
   a second nare having a fixed length,
      a remote free first end of the second nare having a primary inlet/outlet opening therein and being sized to be received within a second nasal passage of the nose, and
      a second end of the second nare being connected to the second compartment of the nasal cannula
   at least a first mouthpiece being connected to the nasal cannula and communicating with the first compartment and a mouth of the patient, whereby a detection device, coupled to the first and second compartments of the nasal cannula, monitors breathing characteristics of a patient while the patient is sleeping through at least one of the primary inlet/outlet opening and the secondary inlet/output opening of at least one of the first and second nares, and
   wherein the nasal cannula is coupled to the detection device by first and second tubes; and a filter prevents moisture from flowing along the first and the second tubes toward the detection device.

15. The nasal cannula for monitoring breathing of a patient according to claim 14, wherein the detection device is electrically connected to polysomnography equipment for inputting measured respiratory air waves and respiratory air flow information, obtained during a sleep diagnostic session.

16. A nasal cannula for monitoring breathing of a patient, the nasal cannula comprising:
   an elongated hollow body for positioning adjacent a nose of the patient,
      the hollow body being divided into first and second compartments;
   a first nare being sized to be received within a first nasal passage of the nose,
   the first nare having a remote free first end having an inlet/outlet opening therein and a second end communicating with the first internal compartment;
   a second nare being sized to be received within a second nasal passage of the nose,
   the second nare having a remote free first end having an inlet/outlet opening therein and a second end communicating with the second internal compartment;
   at least one mouthpiece for communicating with a mouth of the patient to facilitate sensing one of a first or second desired breathing characteristic of a patient, the at least one mouthpiece communicating with one of the first and the second compartments;
   a first tube for coupling the first compartment of the nasal cannula to a first detection device for sensing the first desired breathing characteristic of the patient while the patient is sleeping, via the primary inlet/outlet opening of the first nare; and
   a second tube for coupling the second compartment of the nasal cannula to a second detection device for sensing the second desired breathing characteristic of the patient, while the patient is sleeping, via the primary inlet/outlet opening of the second nare.

17. The nasal cannular for monitoring breathing of a patient according to claim 16, wherein the first and second breathing characteristics of the patient each comprise one of the following functions:
   a) one of sampling and withdrawing an exit gas being exhausted by the patient;
   b) sampling end tidal $CO_2$ in the exhaled gas of the patient;
   c) one of monitoring and detecting the breathing of the patient;
   d) one of monitoring and detecting respiratory air waves and air flow of the patient during breathing; and
   e) detecting changes in pressure within the nostril during breathing of the patient.

18. The nasal cannula for monitoring the detection device by first and second tubes, and a filter prevents moisture from flowing along the first and second tubes toward the detection device.

* * * * *